United States Patent [19]

Yoneyoshi et al.

[11] Patent Number: 4,923,999
[45] Date of Patent: * May 8, 1990

[54] OPTICALLY ACTIVE BORANE COMPLEX AND A METHOD FOR PRODUCING AN OPTICALLY ACTIVE ALCOHOL DERIVATIVE BY THE USE THEREOF

[75] Inventors: Yukio Yoneyoshi, Ootsu; Gohfu Suzukamo, Ibaraki; Kazuhiko Hamada, Nishigyo; Toshio Nishioka, Ashiya, all of Japan

[73] Assignee: Sumitomo Chemical Company, Limited, Osaka, Japan

[ * ] Notice: The portion of the term of this patent subsequent to Jul. 26, 2005 has been disclaimed.

[21] Appl. No.: 169,056

[22] Filed: Mar. 16, 1988

Related U.S. Application Data

[62] Division of Ser. No. 750,255, Jul. 1, 1985, Pat. No. 4,749,809.

[30] Foreign Application Priority Data

Jul. 5, 1984 [JP] Japan ................................ 59-140157

[51] Int. Cl.$^5$ .................. C07D 249/08; C07D 233/60
[52] U.S. Cl. .................... 548/268.4; 548/341
[58] Field of Search ................. 548/262, 341

[56] References Cited

U.S. PATENT DOCUMENTS

| 4,435,203 | 3/1984 | Funaki et al. | 548/262 |
| 4,554,007 | 11/1984 | Funaki et al. | 71/76 |
| 4,760,149 | 7/1988 | Yoneyoshi et al. | 548/262 |

FOREIGN PATENT DOCUMENTS

| 0054431 | 6/1982 | European Pat. Off. |
| 2165400 | 12/1971 | Fed. Rep. of Germany ........ 560/42 |
| 8403885 | 10/1984 | World Int. Prop. O. |

OTHER PUBLICATIONS

Borch et al., J. Org. Chem., vol. 37, No. 14, (1972) 2347.
Itsuno et al. (I), J. Chem. Soc., (1983) pp. 469-470 "Asymmetric Reduction of Aromatic Ketones with the Reagent prepared from (S)-(−)-2-Amino-3-methyl-1,1-diphenylbutan-1-ol and Borane."
Itsuno et al. (II), "Asymmetric Synthesis, etc. (1983) Chemical Abstracts, vol. 100, 22184y (1984)."
Itsuno et al. (III), "Asymmetric Reduction", etc. (1984) Chemical Abstracts, vol. 100, 67806u (1984) [See J. Org. Chem., 49, 555-557 (1984)].
Chemical Abstracts, 97, p. 733, 97: 127690h (1982).
Ferles, M., "Some 1,1-dimethyl-1,2-azaboracycloalkanes, etc." Index Chemicus, 31, 102214 (1968).
Hawthorne, M. F., "Amine Boranes, IX. Dialkylamino Alkylboranes, etc." J.A.C.S., 83, 2671-73 (1961).
Journal of the Chemical Society, Perkin I, 1981, pp. 231-235, Grundon et al. (Asymmetric induction, Part 3.1,2 Asymmetric reduction of ketones ... ).

Primary Examiner—Glennon H. Hollrah
Assistant Examiner—Patricia L. Morris
Attorney, Agent, or Firm—Stevens, Davis, Miller & Mosher

[57] ABSTRACT

The present invention relates to an optically active borane complex represented by the general formula,

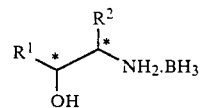

wherein $R^1$ represents an aryl group, $R^2$ represents an alkyl group and a mark * means an asymmetric carbon, and a method for producing optically active alcohol derivatives by the reduction of prochiral ketones with said borane complex. The optically active alcohol derivative is useful for fungicides, herbicides or plant growth regulators.

4 Claims, No Drawings

OPTICALLY ACTIVE BORANE COMPLEX AND A METHOD FOR PRODUCING AN OPTICALLY ACTIVE ALCOHOL DERIVATIVE BY THE USE THEREOF

This is a division of application Ser. No. 750,255, filed July 1, 1985, now U.S. Pat. No. 4,749,809.

The present invention relates to a novel optically active borane complex and a method for producing optically active alcohol derivatives by the use thereof. More particularly, the present invention relates to an optically active borane complex (hereinafter referred to as present compound) represented by the formula (I),

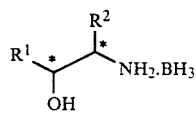

wherein $R^1$ represents an aryl group, $R^2$ represents an alkyl group and a mark * means an asymmetric carbon, and a method for producing optically active alcohol derivatives by the reduction of prochiral ketones with said borane complex.

Alcohol derivatives represented by the formula (IV),

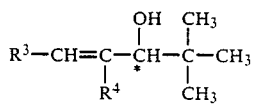

wherein $R^3$ represents a $C_3$-$C_8$ cycloalkyl group which may be substituted with a halogen atom, $C_5$-$C_8$ cycloalkenyl group which may be substituted with a halogen aotm, or phenyl group which may be substituted with a halogen atom, a $C_1$-$C_4$ alkyl, $C_1$-$C_4$ haloalkyl, cyano, $C_1$-$C_4$ alkoxyl, phenoxy or phenyl group, $R^4$ represents an imidazol-1-yl or 1,2,4-triazol-1-yl group and a mark * represents an asymmetric carbon, obtained by the reduction of prochiral ketones, for example, a ketone compound represented by the general formula (III),

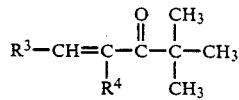

wherein $R^3$ and $R^4$ have the same meanings as described above, are known to be useful as an active ingredient for fungicides, plant growth regulators or herbicides, as represented for example by 1-(2,4-dichlorophenyl)-2-(1,2,4-triazol-1-yl)-4,4-dimethyl-1-penten-3-ol, 1-(4-chlorophenyl)-2-(1,2,4-triazol-1-yl)-4,4-dimethyl-1-penten-3-ol and 1-cyclohexyl-2-(1,2,4-triazol-1-yl)-4,4-dimethyl-1-penten-3-ol [Japanese Patent Application Kokai (Laid-open) Nos. 124771/1980, 100547/1979 and 111477/1980]. And, it is also well known that there is a remarkable difference in the activity between the optical isomers, and that, for example, with reference to the foregoing 1-(2,4-dichlorophenyl)-2-(1,2,4-triazol-1-yl)-4,4-dimethyl-1-penten-3-ol and 1-(4-chlorophenyl)-2-(1,2,4-triazol-1-yl)-4,4-dimethyl-1-penten-3-ol, the (−)-isomer has a strong activity as fungicides, while the (+)-isomer has a strong activity as plant growth regulators and herbicides [Japanese Patent Application Kokai (Laid-open) Nos. 99575/1982 and 106669/1982]. For this reason, there is a demand for the development of a method to produce either one of the (−)- or (+)-optical isomer according to intended uses and yet with a good efficiency in industry.

As the conventionally well-known common reducing agent for reducing the carbonyl group of ketone compounds into alcohol compounds, there are various reagents represented by lithium aluminum hydride and sodium borohydride. But, when these reagents are used, the reduction product obtained is an optically inactive, i.e. racemic compound. Also, when these reagents are used for the reduction of ketone compounds having an unsaturated bond, for example $\alpha,\beta$-conjugated unsaturated ketones, reduction of the double bond in addition to the carbonyl group is easy to occur, and besides there also comes out a possibility that the steric configuration correlated with the double bond is isomerized.

The conventionally well-known reduction of ketone compounds with a borane complex as asymmetric reduction agent is the reduction of acetophenone with an optically active phenethylamine borane complex [Borch, et al., J. Org. Chem., 37, 2347 (1972)], but said reduction gives only a very low optical yield. A borane complex represented by the formula,

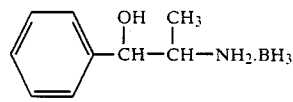

was reported [T. Mancilla, et al., Tetrahedron Letters, 23, 1561 (1982)], but said borane complex is a racemate so that it cannot be used for producing optically active alcohol derivatives as intended by the present invention.

In view of the situation like this, the present inventors extensively studied a method for obtaining optically active alcohol derivatives by the asymmetric reduction of prochiral ketone compounds.

As a result, the present inventors found that when the present compound represented by the foregoing formula (1) is used, the carbonyl group is reduced selectively and stereoisomerization relating to a double bond is strongly depressed, thereby producing the intended optically active alcohol in a high yield. Based on this finding, the present invention has been accomplished.

The present invention will be illustrated in detail hereinafter.

The present compound represented by the foregoing formula (I) is obtained by reacting a salt of an acid with an optically active amino alcohol represented by the formula,

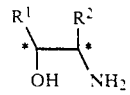

wherein $R^1$, $R^2$ and * are as defined above, with a metal borohydride, followed by hydrolysis of the reaction product.

In the optically active amino alcohol represented by the general formula (II), $R^1$ includes for example a phenyl group which may be substituted with a halogen atom, $C_1$-$C_{10}$ alkyl, cyano, $C_5$-$C_{10}$ cycloalkoxyl, $C_1$-$C_5$ alkoxyl, $C_7$–$C_{11}$ aralkyloxyl, $C_6$–$C_{10}$ aryloxyl or alkoxycarbonyl group, or naphthyl group which may be substituted with a halogen atom, a $C_1$–$C_5$ alkyl, cyano, $C_1$–$C_5$ alkoxyl or alkoxycarbonyl group. Specifically, there are given for example a phenyl, p-tolyl, m-tolyl, o-tolyl, 1-naphthyl, 2,5-dimethylphenyl, 2,5-diethylphenyl, 2,4,6-trimethylphenyl, 2-methoxyphenyl, 2-ethoxyphenyl, 2-propoxyphenyl, 2-isopropoxyphenyl, 2-sec-butoxyphenyl, 2-cyclopentyloxyphenyl, 2-cyclohexyloxyphenyl, 2-benzyloxyphenyl, 2-phenoxyphenyl, 2,4-dimethoxyphenyl, 2,4-diethoxyphenyl, 2,5-dimethoxyphenyl, 2,5-diethoxyphenyl, 2,5-dipropoxyphenyl, 2,5-diisopropoxyphenyl, 2,5-di-n-butoxyphenyl, 2,4,6-trimethoxyphenyl, 2-methoxy-5-methylphenyl, 2-methoxy-5-ethylphenyl, 2-ethoxy-5-methylphenyl, 2-ethoxy-5-ethylphenyl, 2-methoxy-5-t-butylphenyl, 2-ethoxy-5-t-butylphenyl, 2-propoxy-5-methylphenyl, 2-propoxy-5-ethylphenyl, 2-isopropoxy-5-methylphenyl, 2-isopropoxy-5-ethylphenyl, 5-chloro-2-methoxyphenyl, 5-chloro-2-ethoxyphenyl, 5-chloro-2-propoxyphenyl, 5-chloro-2-isopropoxyphenyl, 2-methoxycarbonylphenyl, and 2-ethoxycarbonylphenyl, and the like. $R^2$ includes for example a methyl, ethyl, n-propyl, isopropyl, n-butyl, isobutyl and sec-butyl groups and the like.

Thus, examples of the optically active amino alcohols represented by the general formula (II) are optically active 2-amino-1-phenyl-1-propanol, 2-amino-1-(2,5-dimethylphenyl)-1-propanol, 2-amino-1-(2-methoxyphenyl)-1-propanol, 2-amino-1-(2,5-dimethoxyphenyl)-1-propanol, 2-amino-1-(2,5-diethoxyphenyl)-1-propanol, 2-amino-1-(2-ethoxyphenyl)-1-propanol, 2-amino-1-(2-methoxy-5-methylphenyl)-1-propanol, 2-amino-1-(1-naphthyl)-1-propanol, 2-amino-1-(2-phenoxyphenyl)-1-propanol, 2-amino-1-(2-isopropoxyphenyl)-1-propanol, 2-amino-1-(2-propoxyphenyl)-1-propanol, 2-amino-1-(2-benzyloxyphenyl)-1-propanol, 2-amino-1-(2,4-dimethoxyphenyl)-1-propanol, 2-amino-1-(5-chloro-2-methoxyphenyl)-1-propanol, 2-amino-1-(2,5-dipropoxyphenyl)-1-propanol, and the like.

The optically active amino alcohol represented by the general formula (II) can be produced by optical resolution of a racemic mixture of the active amino alcohol isomers which is prepared, for example, by the method described by W. H. Harting et al. in J. Am. Chem. Soc., 53, pp. 4149–4160 (1931).

The salt of the optically active amino alcohol represented by the general formula (II) with an acid includes for example mineral acid salts (e.g. hydrochloride, sulfate, nitrate, phosphate), carboxylates (e.g. acetate), organic sulfonates (e.g. p-toluenesulfonate) and the like. Said salt may be produced in advance prior to use, or may be formed in situ in the reaction system from the optically active amino alcohol and the acid.

The foregoing metal borohydride includes for example sodium borohydride, potassium borohydride, lithium borohydride, zinc borohydride, etc. Generally, however, the object of the present invention can sufficiently be achieved by using easily available sodium borohydride.

In production of the present compound, the molar ratio of the metal borohydride to the optically active amino alcohol is 0.7:1 to 2:1, preferably 0.7:1 to 1.3:1, more preferably 1:1, as converted to boron basis.

The solvent used in producing the present compound is not particularly limited, so long as it does not take part in the reaction. For example, however, there are given aromatic hydrocarbons (e.g. benzene, toluene, xylene, chlorobenzene), halogenated hydrocarbons (e.g. methylene chloride, 1,2-dichloroethane, chloroform, carbon tetrachloride), and mixtures thereof. Also, in order to dissolve the metal borohydride, for example dimethyl sulfoxide, diglyme, dimethylformamide, 1,3-dimethyl-2-imidazolidinone or the like may be used in combination. The reaction temperature is generally within a range of $-78°$ to $100°$ C., preferably $-40°$ to $100°$ C.

The reaction is generally carried out in an inert gas atmosphere such as nitrogen, argon, etc.

After carrying out the reaction in this way, the present compound can be obtained by adding water to the reaction solution to carry out hydrolysis. Water added for hydrolysis may be neutral or basic like aqueous soidum hdyroxide, etc. The reaction temperature is generally within a range of $0°$ to $60°$ C., preferably $0°$ to $30°$ C.

Besides according to the above-described method, the present compound is obtainable, for example, according to the method of T. Mancilla et al. [Tetrahedron Letters, 23, p. 1561 (1980)] wherein a borane sulfide complex is used. The present compound thus obtained may be purified by the usual operations such as column chromatography.

Next, a method to reduce prochiral ketones using the present compound will be illustrated.

The prochiral ketone includes for example the ketone compound represented by the foregoing formula (III).

The amount of the present compound used in the reduction is not less than 0.3 mole, generally within a range of 0.3 to 2 moles, as converted to boron basis, based on 1 mole of the ketone compound. But, even amounts within a range of 0.5 to 1 mole can sufficiently achieve the object.

Also, the solvent used in the reduction is not particularly limited, so long as it is an inactive solvent. Also, the solvent can contain water. Preferably, however, solvents such as aromatic hydrocarbons (e.g. benzene, toluene, xylene, chlorobenzene), halogenated hydrocarbons (e.g. methylene chloride, 1,2-dichloroethane, chloroform, carbon tetrachloride), ethers (e.g. diethyl ether, tetrahydrofuran, dioxane, diglyme), alcohols (e.g. methanol, ethanol, n-propanol, isopropanol, n-butanol, isobutanol) and mixtures thereof are used. The temperature of the reduction is generally within a range of $-30°$ to $100°$ C., and industrially within a range of $-10°$ to $50°$ C.

After the reduction is carried out in this way, the aqueous solution of a mineral acid (e.g. hydrochloric acid, sulfuric acid) is generally added to the reaction solution to separate into an organic and aqueous layers, the organic layer is washed with water and dried, and then the organic solvent is remvoed by evaporation. By this procedure, the objective optically active alcohol derivative is easily obtained.

The optical purity is obtained by measuring the optical rotation of the product obtained, or directly measuring the enantiomer ratio by high-performance liquid chromatography with optically active packing materials.

Hereupon, the optically active amino alcohol used can easily be recovered, with its steric configuration maintained, by adding an aqueous alkali solution to the aqueous layer after the reaction and extracting with an organic solvent. The recovered optically active amino alcohol can be re-used.

EXAMPLE 1

In a nitrogen atmosphere, 0.338 g of (+)-norephedrine hydrochloride was suspended in 5 ml of chloroform, and after cooling to −30° C., a solution of 0.0681 g of sodium borohydride in 1 ml of dimethylformamide was added. On raising the temperature of the resulting mixture from −30° C. to room temperature over 2 hours, 87 ml of hydrogen gas was generated.

Thereafter, this solution was treated with 2.5N aqueous sodium hydroxide solution, and the organic layer was washed with water and purified by column chromatography on silica gel with a n-hexane/ethyl acetate (1:1) mixture as a developing solvent to obtain 0.112 g of a crystal.

$^{11}$B nuclear magnetic resonance spectrum (standard, BF$_3$.OEt$_2$): −20.5 ppm.

m.p. 93°–95° C. (decomp.).

This crystal, as a result of X-ray analysis, was identified to be a borohydride compound having the following structure:

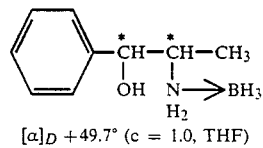

$[\alpha]_D$ +49.7° (c = 1.0, THF)

EXAMPLE 2

Under a nitrogen atmosphere, 0.653 g of (−)-2-amino-1-(2-methoxyphenyl)-1-propanol hydrochloride ($[\alpha]_D$−35.0° (c=1.0, H$_2$O), optical purity 91.0%) was suspended in 7.5 ml of 1,2-dichloroethane. After cooling of the suspension to −20° C., a solution of 0.103 g of sodium borohydride in 1 ml of dimethylformamide was added. The temperature was raised from −20° C. to room temperature over 2 hours. Then the solution was treated with a 2.5N aqueous sodium hydroxide solution. The organic layer was washed with water and purified by column chromatography on silica gel using a n-hexane-ethyl acetate (1:1) mixture as a developing solvent, giving 0.29 g of crystals.

$^{11}$B NMR (standard, BF$_3$.OEt$_2$) δ: −20.5 ppm.

m.p. 108.5°–110° C. (decomp.).

$[\alpha]_D$−49.5° (c=1.1, CHCl$_3$).

EXAMPLE 3–9

Compounds of the general formula (I) were prepared according to the procedure of Example 2 but replacing (−)-2-amino-(2-methoxyphenyl)-1-propanol hydrochloride with (−)-2-amino-1-(2,5-dimethoxyphenyl)-1-propanol hydrochloride ($[\alpha]_D$−27.9° (c=1.0, H$_2$O) optical purity 97.8%), (+)-2-amino-1-(2,5-diethoxyphenyl)-1-propanol hydrochloride ($[\alpha]_D$+29.1° (c=1.0, H$_2$O), optical purity 99% or higher), (+)-2-amino-1-(2-ethoxyphenyl)-1-propanol hydrochloride ($[\alpha]_D$+42.6° (c=1.0, H$_2$O, optical purity 94.2%), (−)-2-amino-1-(2,5-dimethylphenyl)-1-propanol hydrochloride ($[\alpha]_D$−21.0° (c=1.0, H$_2$O), optical purity 98.2%), (−)-2-amino-1-(2-methoxy-5-methylphenyl)-1-propanol hydrochloride ($[\alpha]_D$−22.2° (c=1.0, H$_2$O), optical purity 97.8%), (−)-2-amino-1-(1-naphthyl)-1-propanol hydrochloride ($[\alpha]_D$−33.9° (c=1.0, H$_2$O), optical purity 77.4%), and (+)-2-amino-1-(2-phenoxyphenyl)-1-propanol hydrochloride ($[\alpha]_D$+46.2° (c=0.22, H$_2$O), optical purity 98.2%), respectively.

Data of $^{11}$B NMR spectra, m.p. and specific rotation measured on the obtained optically active amino alcohol-borane complexes are summarized in Table 1.

TABLE 1

| Example No. | Optically active amino alcohol hydrochloride Formula | Charge (g) | Optically active amino alcohol-borane complex Formula | Yield (g) | $^{11}$B NMR (δ ppm) | m.p. (°C.) | $[\alpha]_D$ (CHCl$_3$) |
|---|---|---|---|---|---|---|---|
| 3 | (−) 2,5-(MeO)$_2$-C$_6$H$_3$-CH(OH)-CH(NH$_2$·HCl)-CH$_3$ | 0.67 | (−) 2,5-(MeO)$_2$-C$_6$H$_3$-CH(OH)-CH(N→BH$_3$, H$_2$)-CH$_3$ | 0.36 | −20.5 | 100–102 (decomp.) | −34.3° (C = 0.82) |
| 4 | (+) 2,5-(EtO)$_2$-C$_6$H$_3$-CH(OH)-CH(NH$_2$·HCl)-CH$_3$ | 1.30 | (+) 2,5-(EtO)$_2$-C$_6$H$_3$-CH(OH)-CH(N→BH$_3$, H$_2$)-CH$_3$ | 0.75 | −20.5 | — | +27.0° (C = 1.00) |
| 5 | (+) 2-EtO-C$_6$H$_4$-CH(OH)-CH(NH$_2$·HCl)-CH$_3$ | 0.44 | (+) 2-EtO-C$_6$H$_4$-CH(OH)-CH(N→BH$_3$, H$_2$)-CH$_3$ | 0.25 | −20.4 | 84–87 (decomp.) | +41.3° (C = 0.98) |

TABLE 1-continued

| Example No. | Optically active amino alcohol hydrochloride Formula | Charge (g) | Optically active amino alcohol-borane complex Formula | Yield (g) | $^{11}$B NMR (δ ppm) | m.p. (°C.) | $[α]_D$ (CHCl$_3$) |
|---|---|---|---|---|---|---|---|
| 6 | (−) 3,5-Me$_2$-C$_6$H$_3$-*CH(OH)-*CH(NH$_2$·HCl)-CH$_3$ | 0.54 | (−) 3,5-Me$_2$-C$_6$H$_3$-*CH(OH)-*CH(N H$_2$→BH$_3$)-CH$_3$ | 0.31 | −20.3 | 88–90 (decomp.) | −30.0° (C = 0.49) |
| 7 | (−) 3-Me-4-OMe-C$_6$H$_3$-*CH(OH)-*CH(NH$_2$·HCl)-CH$_3$ | 0.58 | (−) 3-Me-4-OMe-C$_6$H$_3$-*CH(OH)-*CH(N H$_2$→BH$_3$)-CH$_3$ | 0.28 | −20.3 | — | −34.1° (C = 0.86) |
| 8 | (−) 1-naphthyl-*CH(OH)-*CH(NH$_2$·HCl)-CH$_3$ | 0.42 | (−) 1-naphthyl-*CH(OH)-*CH(N H$_2$→BH$_3$)-CH$_3$ | 0.20 | −20.2 | 136.5–138 (decomp.) | −56.4° (C = 0.49) |
| 9 | (+) 2-OPh-C$_6$H$_4$-*CH(OH)-*CH(NH$_2$·HCl)-CH$_3$ | 0.50 | (+) 2-OPh-C$_6$H$_4$-*CH(OH)-*CH(N H$_2$→BH$_3$)-CH$_3$ | 0.26 | −20.5 | 90–92 (decomp.) | +41.3° (C = 0.79) |

EXAMPLE 10

88 Milligrams (0.53 mmole) of the present compound obtained in Example 1 was dissolved in 2 ml of 1,2-dichloroethane, and 2 ml of a 1,2-dichloroethane solution containing 290 mg (1.0 mmole) of (E)-1-(4-chlorophenyl)-2-(1,2,4-triazol-1-yl)-4,4-dimethyl-1-penten-3-one (E/Z=95.8/4.2) was added dropwise thereto. After reaction at room temperature for 24 hours, 2% hydrochloric acid was added to separate the reaction solution into an aqueous and organic layers. After concentrating the organic layer, the residue was purified by column chromatography on silica gel to obtain 180 mg of 1-(4-chlorophenyl)-2-(1,2,4-triazol-1-yl)-4,4-dimethyl-1-penten-3ol. The ratio of E-form alcohol to Z-form alcohol was 95.6 to 4.4, and the enantiomer ratio of the E-form alcohol was: (+)-isomer: (−)-isomer=19:81.

EXAMPLE 11

166 Milligrams (1.02 mmole) of the present compound obtained in Example 1 was dissolved in a 1,2-dichloroethane/dimethylformamide (27 ml/0.5 ml) mixed solvent, and 5 ml of a 1,2-dichloroethane solution containing 975 mg (3.0 mmoles) of (E)-1-(2,4-dichlorophenyl)-2-(1,2,4-triazol-1-yl)-4,4-dimethyl-1-penten-3-one (E/Z=94.8/5.2) was added dropwise thereto. After reaction at room temperature for 16.5 hours, 2% hydrochloric acid was added to separate the reaction solution into an aqueous and organic layers. After concentrating the organic layer, the residue was purified by column chromatography on silica gel to obtain 624 mg of 1-(2,4-dichlorophenyl)-2-(1,2,4-triazol-1-yl)-4,4-dimethyl-1-penten-3-ol. The ratio of the E-form alcohol to Z-form alcohol was 93.8 to 6.2, and the enantiomer ratio of the E-form alcohol was: (+)-isomer: (−)-isomer=18:82.

EXAMPLES 12–30

Each (0.18 mmole) of the present compounds prepared in Examples 2 to 9 was dissolved in 2 ml of a solvent shown in Table 2, and 1.5 ml of a solution of a ketone compound (0.30 mmole) shown in Table 2 in the same solvent was added. After 24 hours' reaction at room temperature, 10% hydrochloric acid was added to the reaction mixture to separate it into two layers. The organic layer was washed with water, dried over Na$_2$SO$_4$, and concentrated under vacuum, giving an optically active alcohol. Results of reactions conducted in this manner are summarized in Table 2.

TABLE 2

| Example No. | Ketone compound | Optically active amino alcohol borane complex | Solvent | Conversion (%) | Composition of reaction product E-form alcohol (%) | Z-form alcohol (%) | Enantiomer ratio of E-form (−)/(+) | Optical[1] yield of E-form (%) |
|---|---|---|---|---|---|---|---|---|
| 12 | 2,4-dichlorophenyl ketone with C(CH₃)₃ and triazole (E/Z = 99.9/0.1) | (2-OMe, 5-MeO phenyl) CH(OH)-CH(NH₂·BH₃)-CH₃ (−) | 1,2-Dichloroethane | 82.4 | 99.7 | 0.3 | 11.4/88.6 | 78.9 |
| 13 | 4-chlorophenyl ketone with C(CH₃)₃ and triazole (E/Z = 98.9/1.1) | " | 1,2-Dichloroethane | 75.4 | 98.1 | 1.9 | 11.2/88.8 | 79.3 |
| 14 | cyclohexyl ketone with C(CH₃)₃ and triazole (E/Z = 99.9/0.1) | (2-OMe, 5-MeO phenyl) CH(OH)-CH(NH₂·BH₃)-CH₃ (−) | 1,2-Dichloroethane | 97.7 | 98.8 | 1.2 | 79.5/20.5 | 60.3 |

TABLE 2-continued

| Example No. | Ketone compound | Optically active amino alcohol borane complex | Solvent | Conversion (%) | Composition of reaction product | | | Optical[1] yield of E-form (%) |
|---|---|---|---|---|---|---|---|---|
| | | | | | E-form alcohol (%) | Z-form alcohol (%) | Enantiomer ratio of E-form (−)/(+) | |
| 15 | 2,4-Cl-C₆H₃-C(=CH-N(imidazole))-C(=O)-C(CH₃)₃ (E/Z = 99.9/0.1) | (−) 2-OMe-C₆H₄-*CH(OH)-*CH(CH₃)-NH₂→BH₃ | 1,2-Dichloroethane | 96.5 | 99.8 | 0.2 | 13.7/86.3 | 79.8 |
| 16 | " | " | Monochlorobenzene | 97.9 | 99.9 | 0.1 | 14.4/85.6 | 78.2 |
| 17 | " | " | Toluene | 96.8 | 99.9 | 0.1 | 14.1/85.9 | 78.9 |
| 18 | " | " | Methanol | 69.1 | 97.5 | 2.5 | 31.8/68.2 | 40.0 |
| 19 | 4-Cl-C₆H₄-C(=CH-N(imidazole))-C(=O)-C(CH₃)₃ (E/Z = 98.9/1.1) | (−) 2-OMe-C₆H₄-*CH(OH)-*CH(CH₃)-NH₂→BH₃ | Monochlorobenzene | 91.9 | 98.5 | 1.5 | 15.7/84.3 | 75.4 |
| 20 | C₆H₁₁-C(=CH-N(imidazole))-C(=O)-C(CH₃)₃ (E/Z = 99.9/0.1) | " | 1,2-Dichloroethane | 99.0 | 98.6 | 1.4 | 76.2/23.8 | 57.6 |

TABLE 2-continued

| Example No. | Ketone compound | Optically active amino alcohol borane complex | Solvent | Conversion (%) | Composition of reaction product | | Enantiomer ratio of E-form (−)/(+) | Optical[1] yield of E-form (%) |
|---|---|---|---|---|---|---|---|---|
| | | | | | E-form alcohol (%) | Z-form alcohol (%) | | |
| 21 | (E/Z = 99.9/0.1) | (+), OEt | 1,2-Dichloroethane | 94.7 | 99.8 | 0.2 | 86.3/13.7 | 77.1 |
| 22 | (E/Z = 98.9/1.1) | (+), OEt | 1,2-Dichloroethane | 84.1 | 98.1 | 1.9 | 85.6/14.4 | 75.6 |
| 23 | (E/Z = 99.9/0.1) | (+), OEt, EtO | 1,2-Dichloroethane | 80.7 | 99.7 | 0.3 | 88.2/11.8 | 76.4 |

TABLE 2-continued
| Example No. | Ketone compound | Optically active amino alcohol borane complex | Solvent | Conversion (%) | Composition of reaction product | | | Enantiomer ratio of E-form (−)/(+) | Optical[1] yield of E-form (%) |
|---|---|---|---|---|---|---|---|---|---|
| | | | | | E-form alcohol (%) | Z-form alcohol (%) | | | |
| 24 | 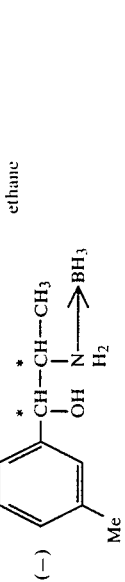 $\left(\dfrac{E}{Z} = \dfrac{99.9}{0.1}\right)$ | 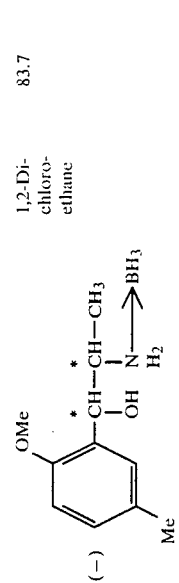 (−) | 1,2-Dichloroethane | 85.4 | 99.7 | 0.3 | | 15.6/84.4 | 70.1 |
| 25 | " | 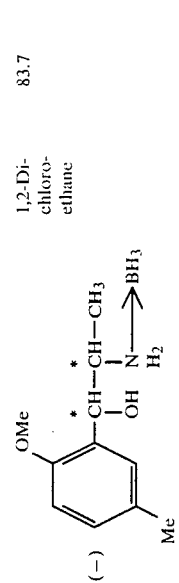 (−) | 1,2-Dichloroethane | 83.7 | 99.7 | 0.3 | | 10.3/89.7 | 81.2 |
| 26 | " | " | Ethanol | 67.4 | 96.4 | 3.8 | | 30.1/69.9 | 40.7 |
| 27 | " | " | Isopropanol | 89.9 | 97.0 | 3.0 | | 19.1/80.9 | 63.2 |
| 28 | " | 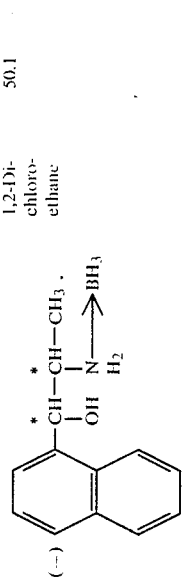 (−) | 1,2-Dichloroethane | 50.1 | 96.2 | 3.8 | | 19.9/80.1 | 77.8 |

TABLE 2-continued

| Example No. | Ketone compound | Optically active amino alcohol borane complex | Solvent | Conversion (%) | Composition of reaction product | | | Optical[1] yield of E-form (%) |
| | | | | | E-form alcohol (%) | Z-form alcohol (%) | Enantiomer ratio of E-form (−)/(+) | |
| --- | --- | --- | --- | --- | --- | --- | --- | --- |
| 29 | 2,4-Cl-C₆H₃–C(=CH–N(imidazole))–C(=O)–C(CH₃)₃  (E/Z = 99.9/0.1) | (−)-2-PhO-C₆H₄–*CH(OH)–*CH(CH₃)–N(H₂)→BH₃ | 1,2-Dichloroethane | 85.6 | 99.8 | 0.2 | 88.6/11.4 | 78.6 |
| 30 | 4-Cl-C₆H₄–C(=CH–N(imidazole))–C(=O)–C(CH₃)₃  (E/Z = 98.9/1.1) | " | 1,2-Dichloroethane | 79.0 | 98.7 | 1.3 | 89.5/10.5 | 80.4 |

Note
[1] The value corrected based on optical purity of the optically active amino alcohol.

What is claimed is:

1. A process for producing optically active alcohol derivatives represented by the formula (IV),

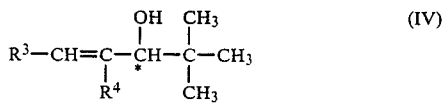

wherein $R^3$ represents a $C_3$-$C_8$ cycloalkyl unsubstituted or substituted by halogen, $C_5$-$C_8$ cycloalkenyl unsubstituted or substituted by halogen, or phenyl unsubstituted or substituted by at least one member selected from the group consisting of halogen, $C_1$-$C_4$ alkyl, $C_1$-$C_4$ haloalkyl, cyano, $C_1$-$C_4$ alkoxy, phenoxy and phenyl, $R^4$ represents an imidazol-1-yl or 1,2,4-triazol-1-yl group, and the mark * represents an asymmetric carbon, which comprises reducing a prochiral ketone represented by the formula (III),

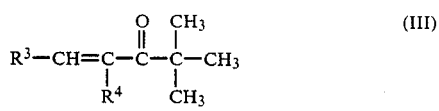

wherein $R^3$ represents a $C_3$-$C_8$ cycloalkyl unsubstituted or substituted by halogen, $C_5$-$C_8$ cycloalkenyl unsubstituted or substituted by halogen, or phenyl unsubstituted or substituted by at least one member selected from the group consisting of halogen, $C_1$-$C_4$ alkyl, $C_1$-$C_4$ haloalkyl, cyano, $C_1$-$C_4$ alkoxy, phenoxy and phenyl, $R^4$ represents an imidiazol-1-yl or 1,2,4-triazol-1-yl with an active borane complex represented by the formula (I),

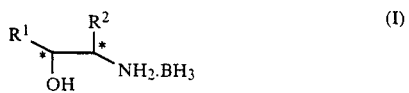

wherein $R^1$ represents phenyl unsubstituted or substituted by at least one of halogen, $C_1$-$C_{10}$ alkyl, cyano, $C_5$-$C_{10}$ cycloalkoxy, $C_1$-$C_5$ alkoxy, $C_7$-$C_{11}$ aralkyloxy, $C_6$-$C_{10}$ aryloxy and $C_1$-$C_3$ alkoxycarbonyl, or naphthyl unsubstituted or substituted by at least one of halogen, $C_1$-$C_5$ alkyl, cyano, $C_1$-$C_5$ alkoxy and $C_1$-$C_3$ alkoxycarbonyl, $R^2$ represents $C_1$-$C_5$ alkyl and the mark * means an asymmetric carbon.

2. The process of claim 1, wherein the optically active borane complex represented by the formula (I) is obtained by reacting a salt of an acid with an optically active amino alcohol represented by the general formula,

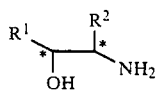

wherein, $R^1$ represents phenyl unsubstituted or substituted by at least one of halogen, $C_1$-$C_{10}$ alkyl, cyano, $C_5$-$C_{10}$ cycloalkoxy, $C_1$-$C_5$ alkoxy, $C_7$-$C_{11}$ aralkyloxy, $C_6$-$C_{10}$ aryloxy and $C_1$-$C_3$ alkoxycarbonyl, or naphthyl unsubstituted or substituted by at least one of halogen, $C_1$-$C_5$ alkyl, cyano, $C_1$-$C_5$ alkoxy and $C_1$-$C_3$ alkoxycarbonyl, $R^2$ represents $C_1$-$C_5$ alkyl and a mark * means an asymmetric carbon, with a metal borohydride, followed by hydrolysis of the reaction product.

3. The process of claim 1, wherein $R^1$ in the formula (I) is a 2,5-dimethoxyphenyl, 2,5-diethoxyphenyl, 2-methoxyphenyl, 2-ethoxyphenyl, 2-methoxy-5-methylphenyl, 2-methoxyphenyl, 2-ethoxyphenyl, 2-methoxy-5-methylphenyl, 2,5-dimethylphenyl, 2-phenoxyphenyl, phenyl or naphthyl group.

4. The process of claim 1, wherein the prochiral ketone is 1-(2,4-dichlorophenyl)-2-(1,2,4-triazol-1-yl)-4,4-dimethyl-1-penten-3-one, 1-(4-chlorophenyl)-2-(1,2,4-triazol-1-yl)-4,4-dimethyl-1-penten-3-one or 1-cyclohexyl-2-(1,2,4-triazol-1-yl)-4,4-dimethyl-1-penten-3-one.

* * * * *